US009901477B2

(12) United States Patent
Tu

(10) Patent No.: US 9,901,477 B2
(45) Date of Patent: Feb. 27, 2018

(54) TRACTION DEVICE FOR NECK PHYSICAL THERAPY

(71) Applicant: Feng Ching Tu, New Taipei (TW)

(72) Inventor: Feng Ching Tu, New Taipei (TW)

( * ) Notice: Subject to any disclaimer, the term of this patent is extended or adjusted under 35 U.S.C. 154(b) by 335 days.

(21) Appl. No.: 14/515,374

(22) Filed: Oct. 15, 2014

(65) Prior Publication Data

US 2016/0106566 A1    Apr. 21, 2016

(51) Int. Cl.
*A61F 5/042* (2006.01)
*A61H 1/02* (2006.01)

(52) U.S. Cl.
CPC .......... *A61F 5/042* (2013.01); *A61H 1/0296* (2013.01); *A61H 2201/0142* (2013.01); *A61H 2201/149* (2013.01); *A61H 2201/1604* (2013.01); *A61H 2201/1611* (2013.01); *A61H 2201/1614* (2013.01); *A61H 2201/5043* (2013.01); *A61H 2205/04* (2013.01)

(58) Field of Classification Search
CPC ...... A61F 5/00; A61F 5/01; A61F 5/04; A61F 5/042; A61F 5/048; A61H 1/02; A61H 1/0218; A61H 1/0292; A61H 1/0296; A61H 2201/1609; A61H 2201/1611
USPC ............................................ 602/32, 36, 40
See application file for complete search history.

(56) References Cited

U.S. PATENT DOCUMENTS

| | | | |
|---|---|---|---|
| 6,899,690 B2 | 5/2005 | Saunders et al. | |
| 2014/0221895 A1* | 8/2014 | Bonutti | A61F 5/042 602/36 |
| 2016/0015549 A1* | 1/2016 | Thomas | A61F 5/3707 602/36 |

* cited by examiner

Primary Examiner — Keri J Nelson
(74) *Attorney, Agent, or Firm* — Muncy, Geissler, Olds & Lowe, P.C.

(57) ABSTRACT

A traction device for neck physical therapy includes a control unit, a knob unit having a transmission disc, a knob and a force applying cable, and the transmission disc and the knob being pivotally installed at the control unit, and the knob being linked to a transmission shaft, and an end of the force applying cable being fixed to the transmission disc; a body unit; a force indication unit, including a load positioning module, an elastic member, a thrust cable and an indicator, and the load positioning module being installed in the body unit and linked to the force applying cable, and the elastic member having two fixing ends, one being fixed to the load positioning module, and the thrust cable being coupled to the load positioning module and the indicator; and a transfer unit, fixed to the load positioning module and slidably installed on the body unit.

10 Claims, 12 Drawing Sheets

TRACTION DEVICE FOR NECK PHYSICAL THERAPY

FIELD OF THE INVENTION

The present invention relates to a traction device for neck physical therapy, and more particularly to the traction device for physical therapy that facilitates patients to operate the device on their own, control the applied force, and view the status of the traction force.

BACKGROUND OF THE INVENTION

In general, a traction machine is usually directed to physical therapy treatments for neck, spine or back pain and used to stretch muscle tissues to straighten or reduce the curvature of a patient's back or neck, so as to relieve the pain or achieve the treatment and recovery effects. With reference to FIG. 1 for a conventional traction machine for physical therapy treatment for a neck pain, the traction machine comprises a traction base 91, a neck base 92 and a headrest portion 93 disposed at an end of the traction base 91, a pushing portion 94 disposed at another end of the traction base 91 and linked with the neck base 92 and the headrest portion 93, and a pneumatic cylinder 95 installed at the bottom of the traction base 91 and abutted and coupled to the pushing portion 94. In addition, a mat portion 96 is disposed on an outer side of the neck base 92. While using the equipment, a patient lies on the mat portion 96 and positions the neck on the neck base 92 and the head on the headrest portion 93. Now, the patient may operate a pusher (not shown in the figure), and the pusher links and controls the operation of the pneumatic cylinder 95 by an air pipe 951, and the pneumatic cylinder 95 is operated to push the pushing portion 94 and drive the neck base 92 and headrest portion 93 to move in order to achieve the neck traction effect. Related prior arts have been disclosed in U.S. Pat. No. 6,899,690, PRC Pat. No. 1943527, etc.

Although the aforementioned conventional traction machine can achieve the traction effect, it still has the following drawbacks: The patients operates a pusher to control the operation of the pneumatic cylinder 95, wherein the pusher is similar to a pump, and the patient has to push the pusher reciprocally to pump air, and thus the traction operation is very inconvenient. In addition, it is difficult to control the applied force and load. An end of the pusher generally has a force indicator (or force indicating meter) for indicating a traction force or load (in pounds), so that the patient can know about the traction force or load (in pounds) through the force indicator during the traction operation. The patient can view the force indicator after operating the pusher reciprocally for a while, but cannot perform an appropriate traction operation while viewing the force indicator, or cannot view a change of the force indicator while performing the traction operation and use the force applied for the traction operation as a reference. Obviously, the conventional traction machine requires further improvements. Therefore, it is an important subject for related manufacturers to overcome the drawbacks of the conventional traction machine.

In view of the drawbacks of the conventional traction machine, the inventor of the present invention based on years of experience in the related industry to conduct extensive researches and experiments, and finally developed a traction device for neck physical therapy with a convenient operation, a high controllability on applying force, and a function of simultaneously viewing and operating the traction machine in accordance with the present invention.

SUMMARY OF THE INVENTION

Therefore, it is a primary objective of the present invention to provide a traction device for neck physical therapy that facilitates users to operate the traction device on their own, control the traction force, and make fine-tune adjustments easily.

Another objective of the present invention is to provide a traction device for neck physical therapy that allows users to view the change of the indicator while using the traction device to perform a traction operation, and use such change as a reference for the force applied in the traction operation, or perform an appropriate fine-tune operation of the traction while viewing the indicator, so as to achieve excellent operability, comfortability and safety of the traction device.

To achieve the aforementioned objectives, the present invention provides a traction device for neck physical therapy, comprising: a control unit, including a controller casing; a knob unit, including a transmission disc, a knob and a force applying cable, and the transmission disc being pivotally installed in the controller casing, and the knob being installed onto the controller casing, and linked to a transmission shaft, and the transmission shaft being linked with the transmission disc, and an end of the force applying cable being fixed to the transmission disc; a body unit, including a casing comprised of a lower casing and an upper casing; a force indication unit, including a load positioning module, an elastic member, a thrust cable and an indicator, and the load positioning module being installed in the casing, and the load positioning module being coupled to an end of the force applying cable opposite to the transmission disc, and the elastic member having a first fixing end and a second fixing end, and the first fixing end being fixed to the load positioning module, and the second fixing end being positioned in the body unit, and an end of the thrust cable being coupled to the load positioning module, and the other end of the thrust cable being coupled to the indicator, and the indicator being installed onto the control unit; and a transfer unit, fixed to the load positioning module and slidably installed on the body unit.

Wherein, the controller casing includes a casing perforation formed thereon, and the transmission shaft is pivotally installed in the controller casing and linked by the connection of the casing perforation and the knob, and the controller casing includes an accommodating groove for installing the knob, and a viewing slot.

Wherein, the transmission disc and the transmission shaft respectively have gear ends disposed at peripheries of the transmission disc and the transmission shaft and coupled to each other, and a cable collection slot is formed at the periphery of the transmission disc, and the force applying cable is fixed into the cable collection slot.

Wherein, the knob unit further comprises a positioning plate fixed into the controller casing, and the positioning plate includes a convex positioning seat protruded from the casing perforation and having a shaft hole.

Wherein, the knob unit further comprises a stablizing member fixed into the controller casing, and the stablizing member includes a gear member pivotally coupled to the gear end, and the gear member has an elastic resistance.

Wherein, the knob unit further comprises an elastic pressing member, and the controller casing includes a plurality of positioning notches formed on the elastic pressing member, and an end of the elastic pressing member is abutted against a tooth end of the gear portion of the knob, and the bottom of the elastic pressing member is abutted by a spring.

Wherein, the casing includes a solder connecting portion disposed at an end of the casing and a pivotal support stand coupled to the other end of the casing, and the solder connecting portion is in an outwardly oblique tapered shape.

Wherein, the upper casing includes a long slot longitudinally penetrated through the upper casing, and the load positioning module is passed through the long slot and coupled to a headrest.

Wherein, the upper casing includes a rolling slot formed at the top of the upper casing and separately disposed on both sides of the long slot, and a containing groove is formed separately on both sides of the bottom of the upper casing.

Wherein, the load positioning module comprises a distal connecting member, a support member and a linking member, and the distal connecting member is coupled to the force applying cable and the thrust cable, and the second fixing end of the elastic member is coupled to the distal connecting member.

Wherein, the distal connecting member includes a backwardly protruded pushrod, and the support member includes a pushing groove for containing and abutting the pushrod.

Wherein, the linking member and the support member are fixed to each other, and the headrest is passed through the long slot and coupled to the linking member.

Wherein, the solder connecting portion includes a dolly fixed therein, and the dolly includes a wheel coupled to a buffer strip, and an end of the buffer strip is coupled to the second fixing end of the elastic member.

Wherein, the indicator includes a display block and a viewing panel coupled to the thrust cable, and the display block is linked to a pointer.

The present invention will become clearer in light of the following detailed description of an illustrative embodiment of this invention described in connection with the drawings.

DESCRIPTION OF THE PREFERRED EMBODIMENTS

Figure 1:
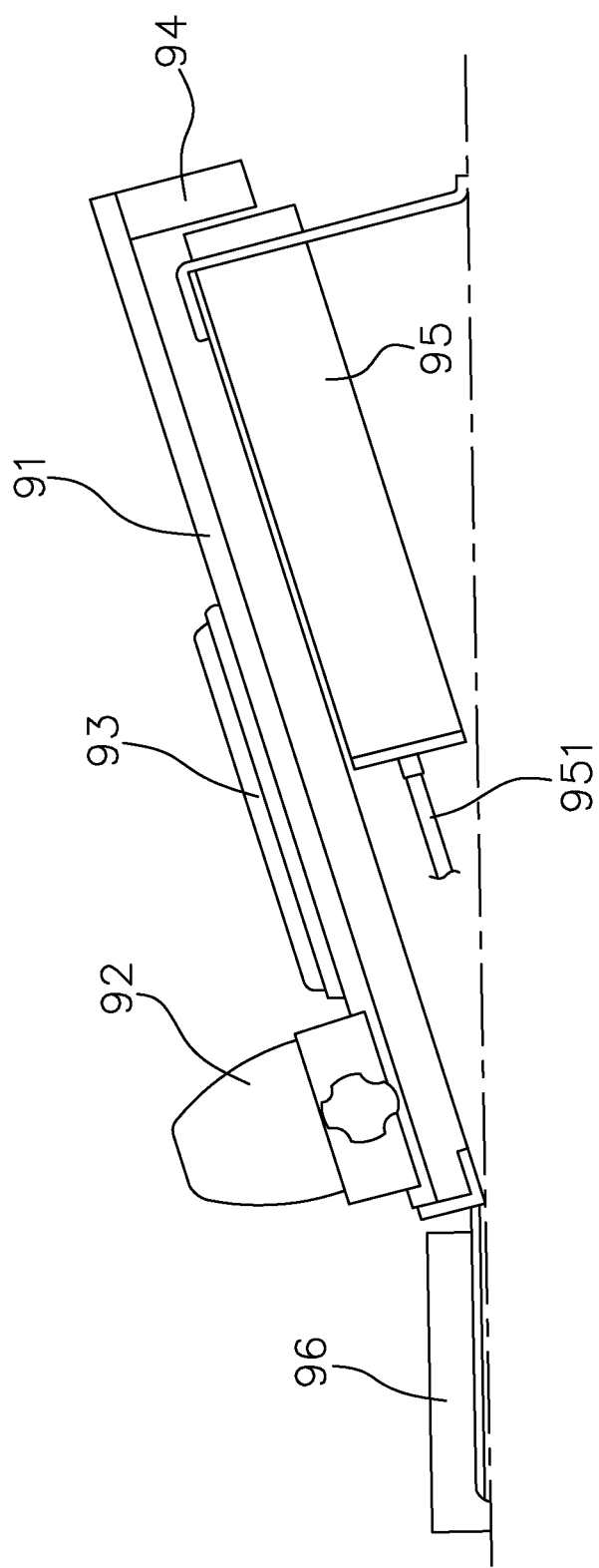
FIG. 1 is a schematic view of a conventional traction device.
Figure 2:
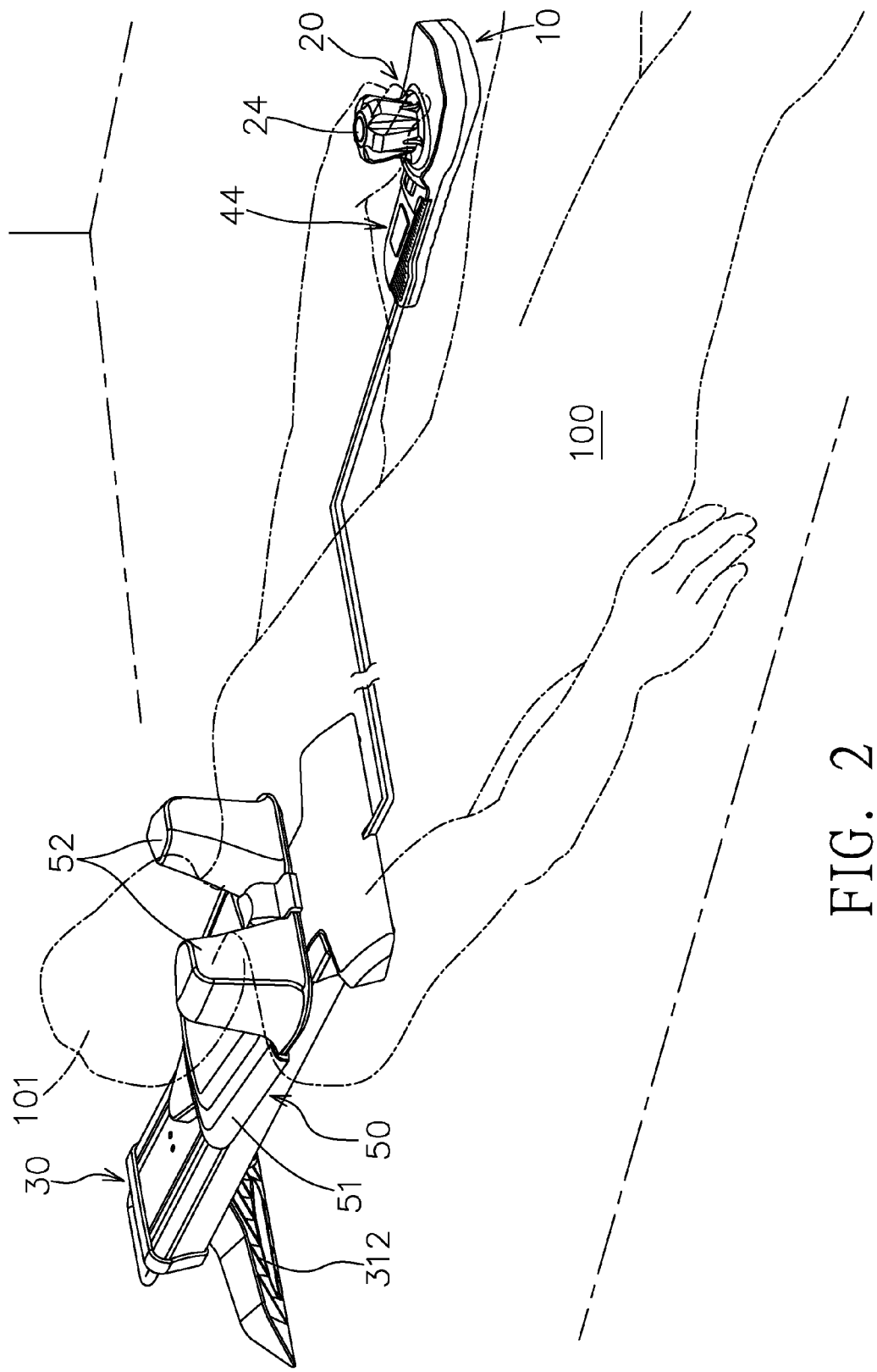
FIG. 2 is a schematic view of an application of the present invention.
Figure 3:
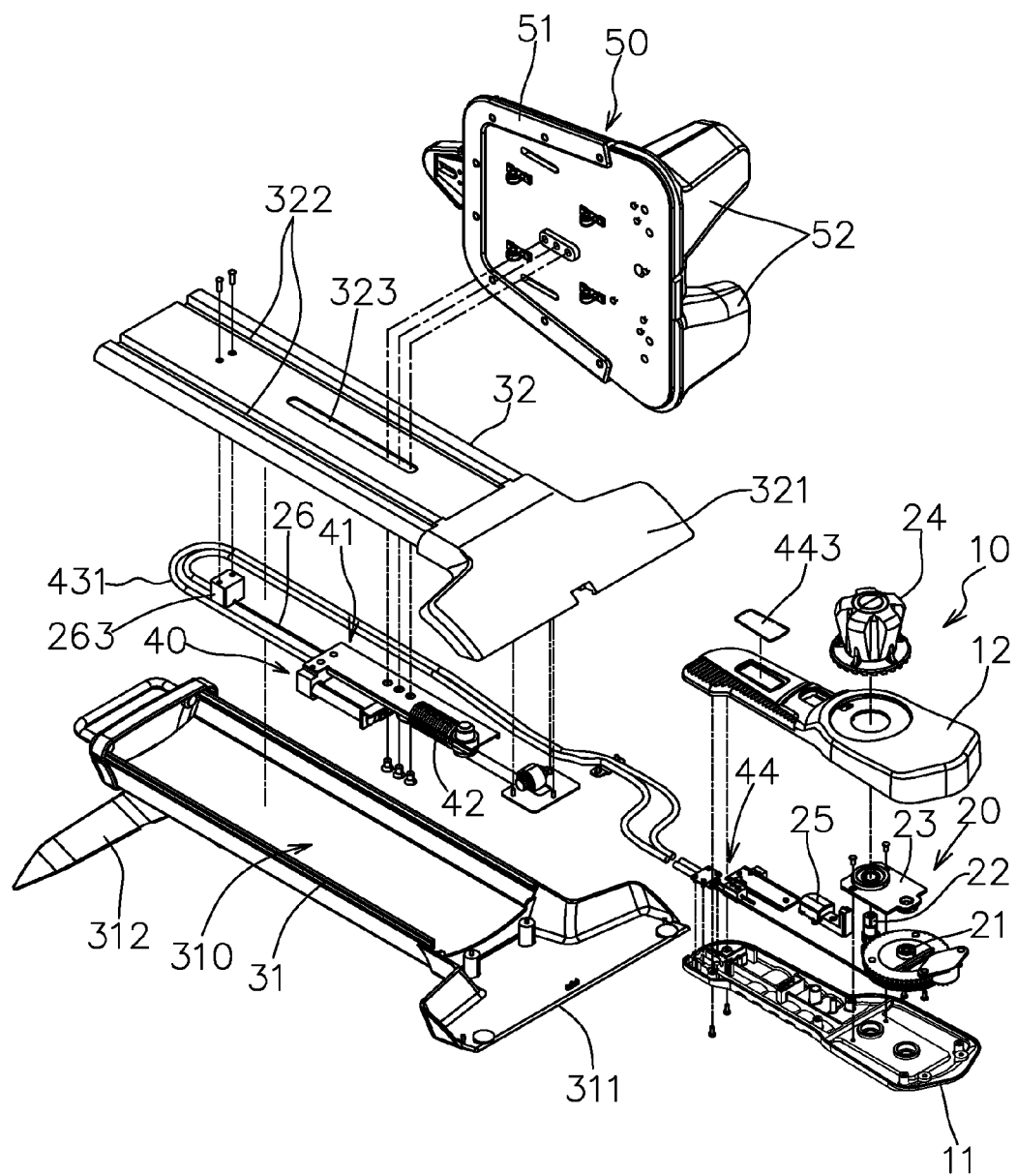
FIG. 3 is an exploded view of the present invention.

With reference to FIGS. 2 and 3 for a traction device for neck physical therapy in accordance with the present invention, a neck tractor is used as an embodiment for illustrating the invention. The traction device comprises: a control unit 10, a knob unit 20, a body unit 30, a force indication unit 40 and a transfer unit 50. In FIGS. 2 and 3, the body unit 30 is in an obliquely installed status, and a user 100 may place the user's head 101 on the transfer unit 50 while turning a knob unit 20 (or a knob) installed on the control unit 10 to push the transfer unit 50, so as to achieve a neck traction effect.

Figure 4:
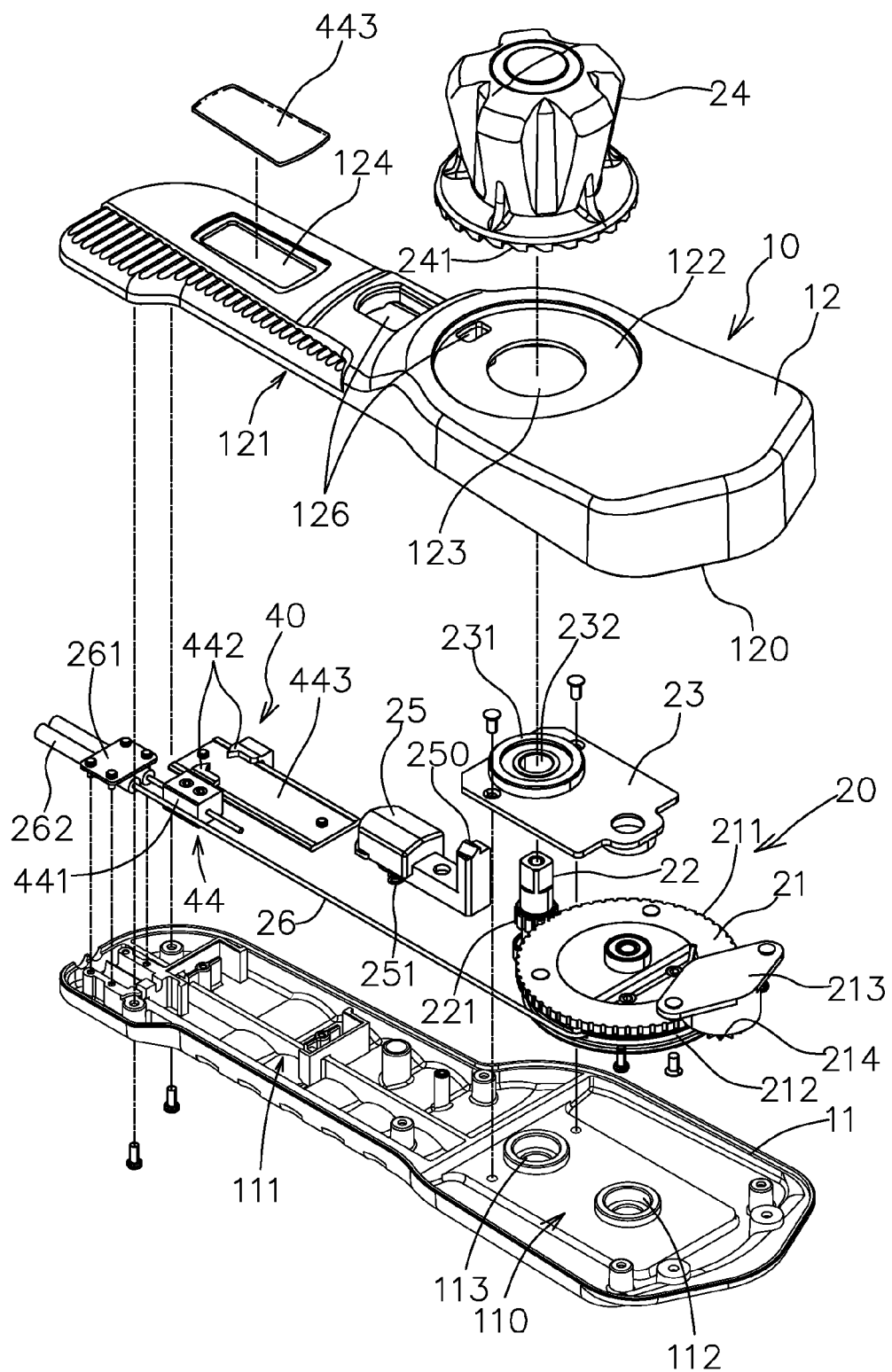
FIG. 4 is a first partial exploded view of the present invention.

With reference to FIG. 4, the control unit 10 includes a lower controller casing 11 and an upper controller casing 12 which are engaged with each other to form a controller casing. The lower controller casing 11 includes a bottom operation space 110 and a handle space 111 formed therein, and the bottom operation space 110 includes a first shaft hole seat 112 and a second shaft hole seat 113 disposed therein; and the upper controller casing 12 includes a top operation space 120 and a handle space 121 disposed therein, and the upper controller casing 12 has an accommodating groove 122 and a viewing slot 124 (or viewing window), and the accommodating groove 122 has a casing perforation 123 penetrated through the top operation space 120, and the upper controller casing 12 has a plurality of positioning notches 126 formed thereon.

Figure 5:
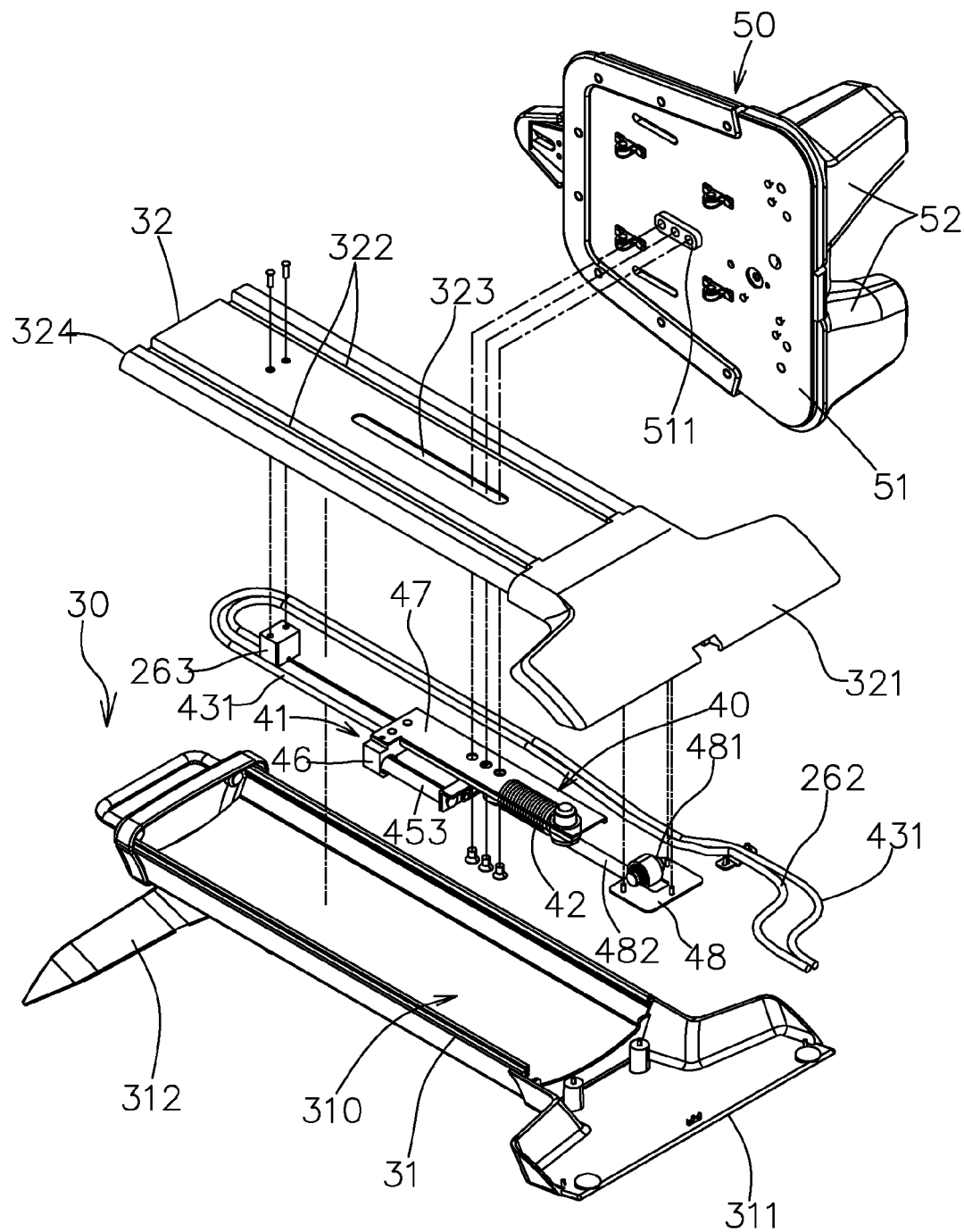
FIG. 5 is a second partial exploded view of the present invention.
Figure 6:
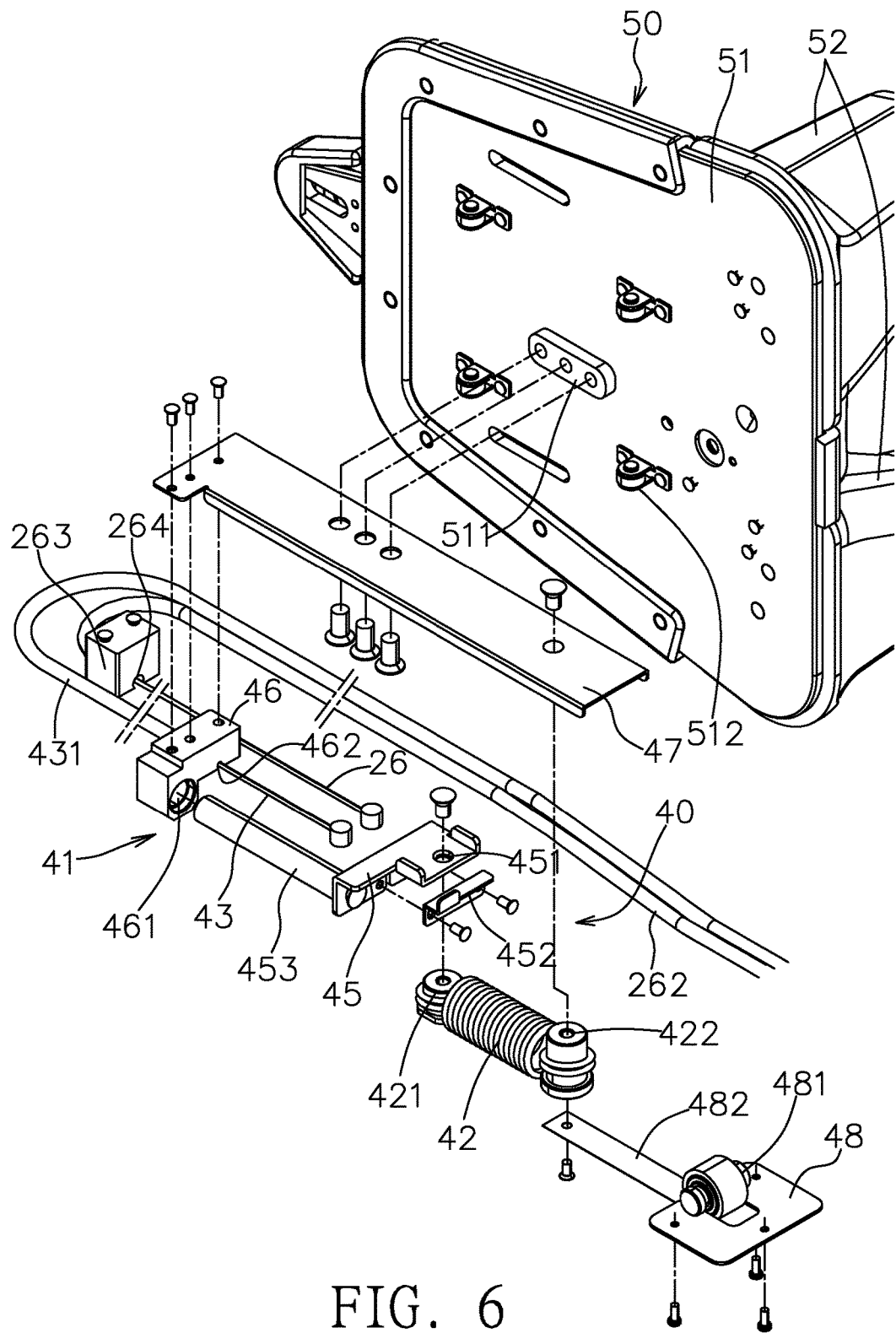
FIG. 6 is a third partial exploded view of the present invention.

The knob unit 20 includes a transmission disc 21, a transmission shaft 22, a positioning plate 23, a knob 24 and a force applying cable 26. The transmission disc 21 is pivotally installed to the first shaft hole seat 112 by its central bottom shaft (not shown in the figure), and the periphery of the transmission disc 21 has a gear end 211 and a cable collection slot 212. The transmission shaft 22 is pivotally installed to the second shaft hole seat 113 by its central bottom shaft, and the periphery of the transmission shaft 22 has a gear end 221 coupled to the gear end 211. The positioning plate 23 is fixed in the bottom operation space 110, and the positioning plate 23 has a convex positioning seat 231 protruded out from the casing perforation 123 for installing the knob 24, and the convex positioning seat 231 has a shaft hole 232. The knob 24 is installed onto the accommodating groove 122 of the upper controller casing 12, and the periphery of the bottom of the knob 24 has a gear portion 241. Wherein, the transmission shaft 22 is passed through the shaft hole 232 and the casing perforation 123 and coupled to the knob 24, so that the knob 24 may be linked and further rotate the transmission shaft 22. The transmission disc 21 has a stablizing member 213 installed on the other side opposite to the transmission shaft 22 and fixed into the bottom operation space 110, and the bottom edge of the stablizing member 213 has a gear member 214 coupled to the gear end 211, and the gear member 214 may be pivoted and has an elastic resistance for balancing and stabilizing the rotation of the transmission disc 21, and an end of the force applying cable 26 is fixed to the cable collection slot 212 of the transmission disc 21, and the other end of the force applying cable 26 is extended and coupled to the force indication unit 40, and a vast majority of the force applying cable 26 is passed through a protective cable 262 to facilitate its wire layout and installation, and the protective cable 262 at an end in the handle space 111 may be positioned by a positioning member 261. The force applying cable 26 (or the protective cable 262) is passed into the body unit 30 as shown in FIGS. 5 and 6, and the body unit 30 further includes a positioning block 263 disposed at an appropriate position therein, and the positioning block 263 includes a cable accommodating groove 264 for passing and positioning the force applying cable 26. In addition, an elastic pressing member 25 is installed at the positioning notch 126, and an end of the elastic pressing member 25 has a tooth end 250, and a spring 251 is abutted at the bottom of the elastic pressing member 25, so that the tooth end 250 is always elastically abutted against the gear portion 241 of the knob 24 to provide an obvious hand feel of the rotation of the knob 24.

Figure 7:
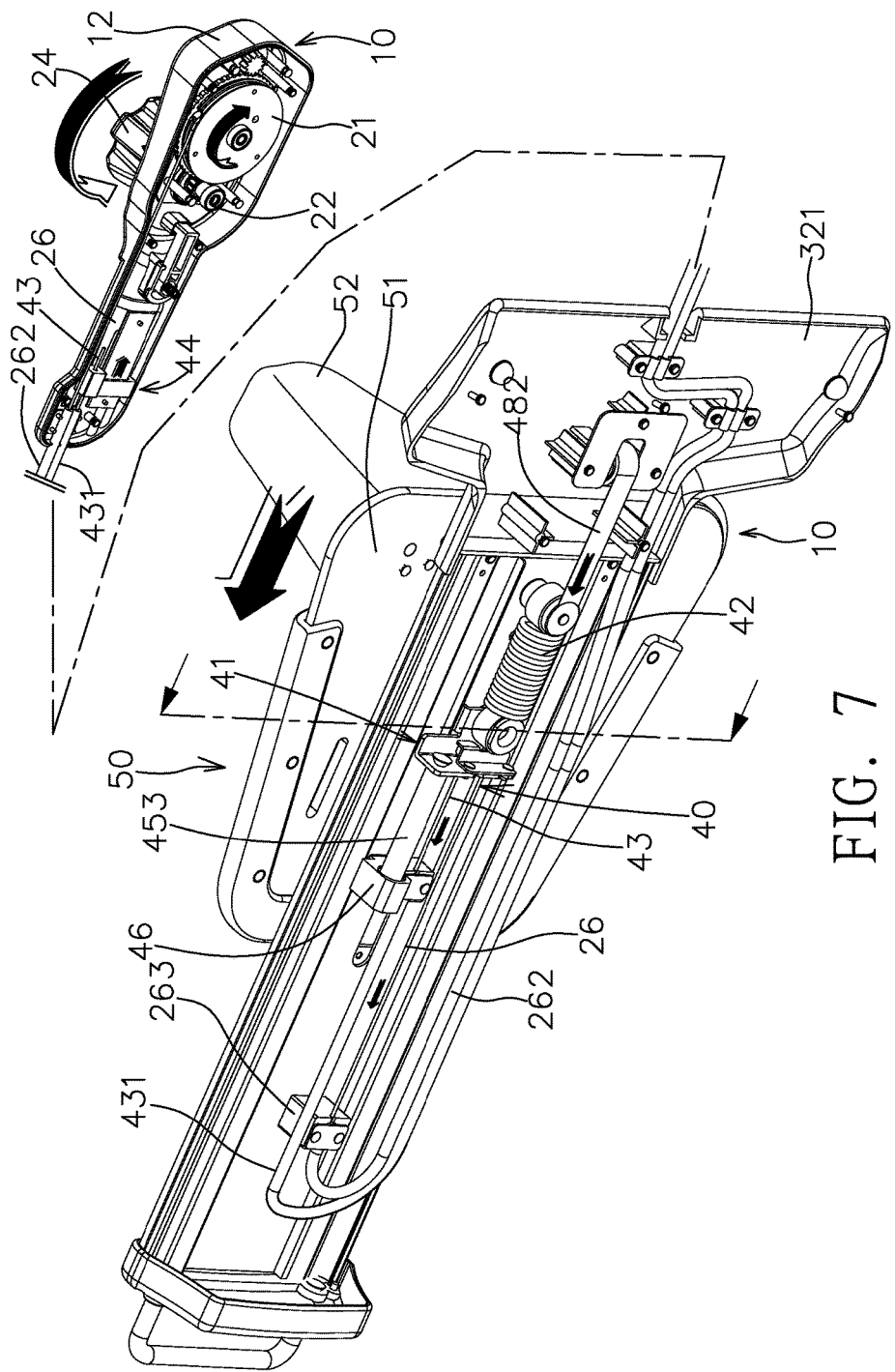
FIG. 7 is a perspective view of the present invention.
Figure 7A:
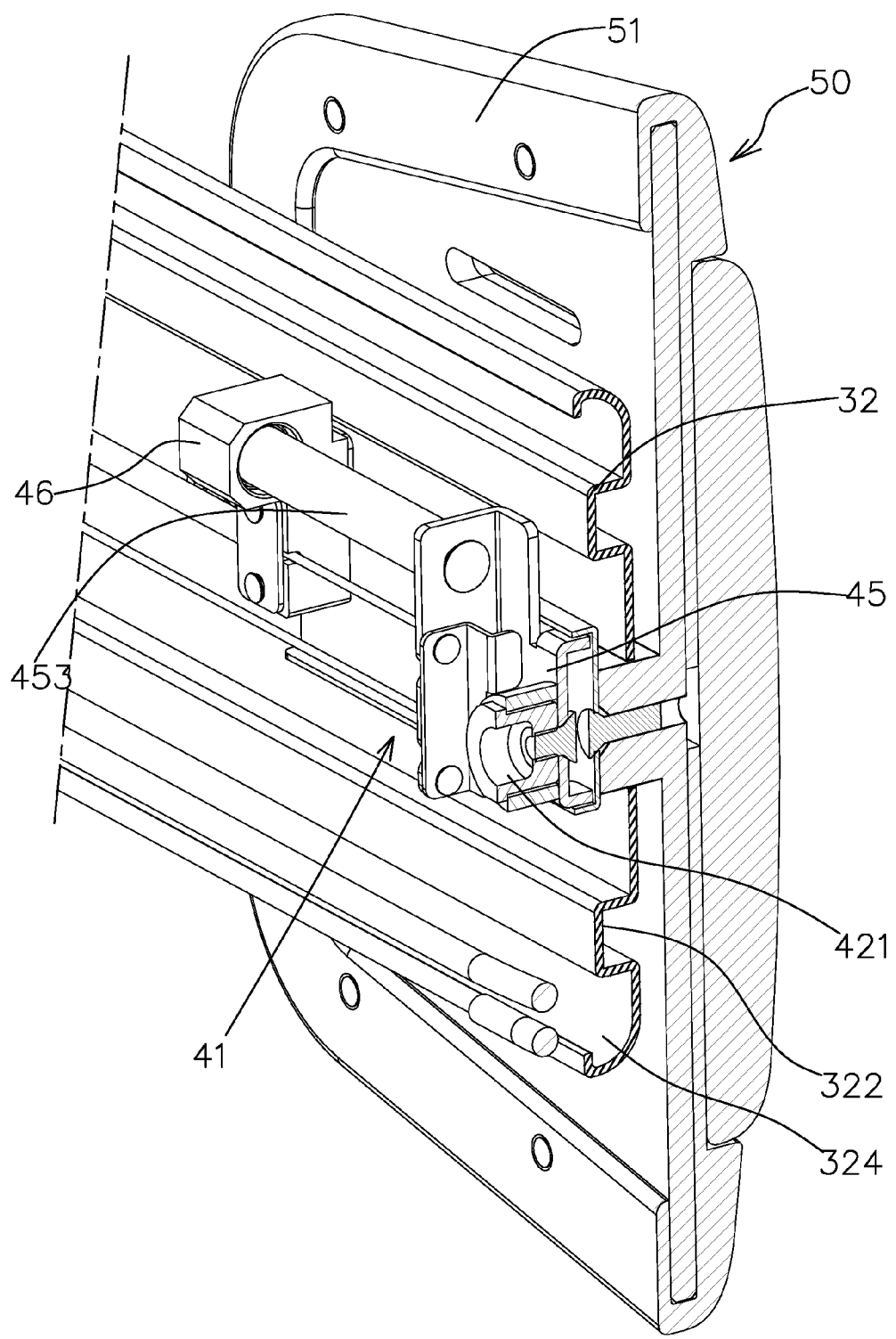
FIG. 7A is a cross-sectional view of the dotted-line section of FIG. 7.
Figure 8:
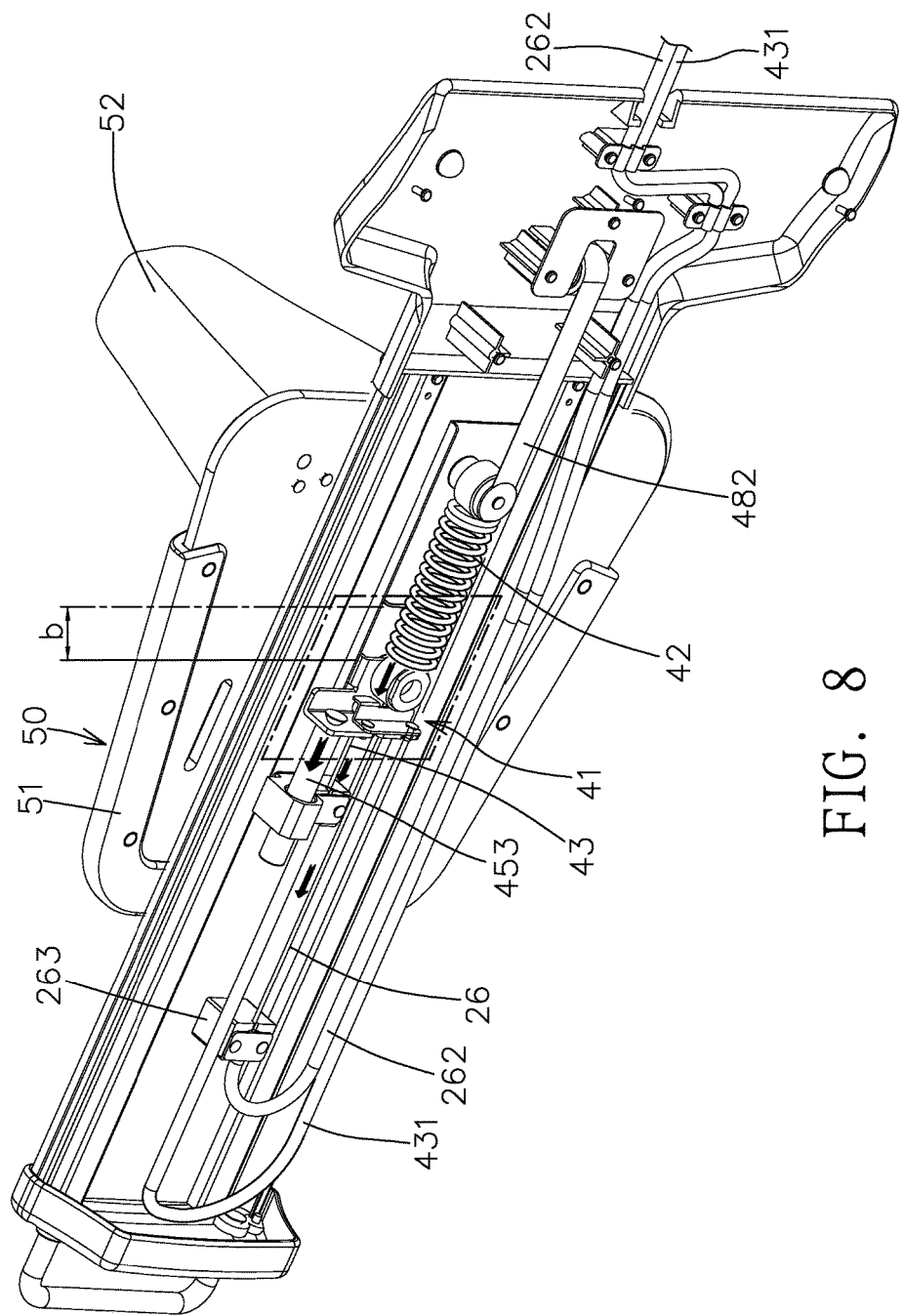
FIG. 8 is a partial perspective view of the present invention.

In FIG. 5, the body unit 30 includes a lower casing 31 and an upper casing 32 engaged with each other to form a casing. The lower casing 31 includes a body chamber 310, and a solder connecting portion 311 is disposed at an end of the lower casing 31 and a pivotal support stand 312 is installed at the other end of the lower casing 31, and the solder connecting portion 311 is in an outwardly oblique tapered shape. The pivotal support stand 312 may be rotated for use or storage. The upper casing 32 has a solder connecting portion 321 disposed at an end of the upper casing 32 and configured to be corresponsive to the solder connecting portion 311 of the lower casing 31, and a penetrating long slot 323 is formed at the central position of the upper casing 32 and in a longitudinal direction, and the top of the upper casing 32 has a rolling slot 322 formed separately on both sides of the long slot 323, and a containing groove 324 formed separately on both sides of the bottom of the upper casing 32 for providing a cable containing space as shown in FIG. 7A.

With reference to 3 to 6, the force indication unit 40 includes a load positioning module 41, an elastic member 42, a thrust cable 43 and an indicator 44, and the load positioning module 41 is coupled to the force applying cable 26, the elastic member 42 and the thrust cable 43 for applying a force or a load and providing a pushing force to provide a traction effect. The load positioning module 41 is installed in the body chamber 310 (or the casing) and the load positioning module 41 further includes a distal connecting member 45, a support member 46 and a linking member 47. The distal connecting member 45 includes a fixing hole 451 and a backwardly protruded pushrod 453, and the distal connecting member 45 is provided for coupling the force applying cable 26 and the thrust cable 43 and fixed into a position by a fixing member 452. In other words, the force applying cable 26, the thrust cable 43 and the elastic member 42 are connected by the distal connecting member 45 (or the load positioning module 41) to produce a traction effect for applying a force or a load and providing a pushing force in an opposite direction. The support member 46 includes a pushing groove 461 and a cable accommodating groove 462, and the pushing groove 461 is provided for installing and abutting the pushrod 453, and the cable accommodating groove 462 is provided for receiving and positioning the thrust cable 43. The linking member 47 is substantially in the shape of a plate and fixed to the support member 46 by a screw connection as shown in the figures. The elastic member 42 is installed in the body chamber 310, wherein the elastic member 42 includes but not limited to a spring. Both ends of the elastic member 42 are a first fixing end 421 and a second fixing end 422 respectively, and the first fixing end 421 is fixed (or screwed as shown in FIG. 7A) into the fixing hole 451 of the distal connecting member 45, and the second fixing end 422 is fixed into the body unit 30 (or the casing) to provide the force applying and pushing effects of the elastic member 42. In this preferred embodiment, the solder connecting portion 321 at the front of the elastic member 42 includes a dolly 48, and the dolly 48 has a wheel 481 coupled to a buffer strip 482 (or a buffer cable), and an end of the buffer strip 482 is fixed (or screwed) to the second fixing end 422 of the elastic member 42, so that the dolly 48 (or the buffer strip 482) which is equivalent to fixing the second fixing end 422 of the elastic member 42 into the body chamber 310. The buffer strip 482 (or the buffer cable) further provides a buffering effect before applying a force to the elastic member 42 to produce a pushing force. The thrust cable 43 is preferably a steel cable having an end coupled to and pushed by the distal connecting member 45 (or the load positioning module 41), and pushed, and the other end coupled to the indicator 44, and a protective cable 431 is sheathed on the thrust cable 43.

Figure 9:
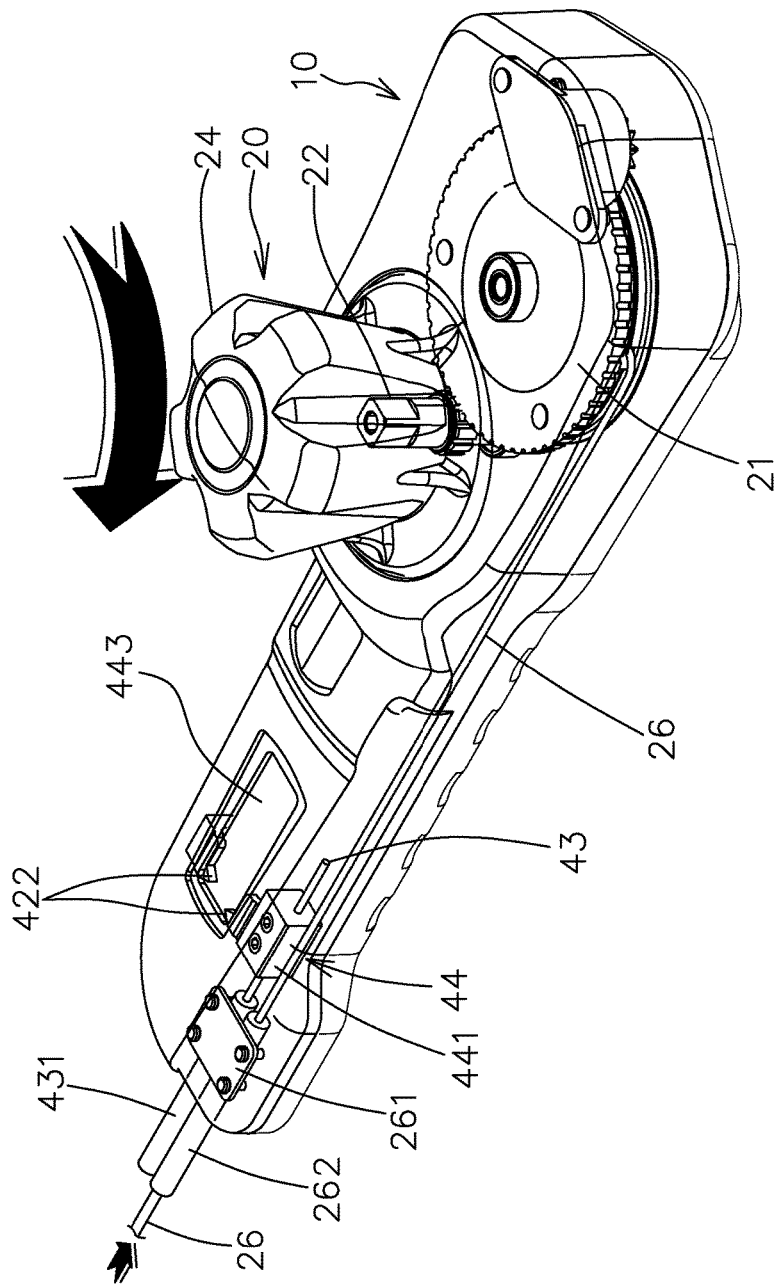
FIG. 9 is a first schematic view of operating and controlling a traction device of the present invention.
Figure 10:
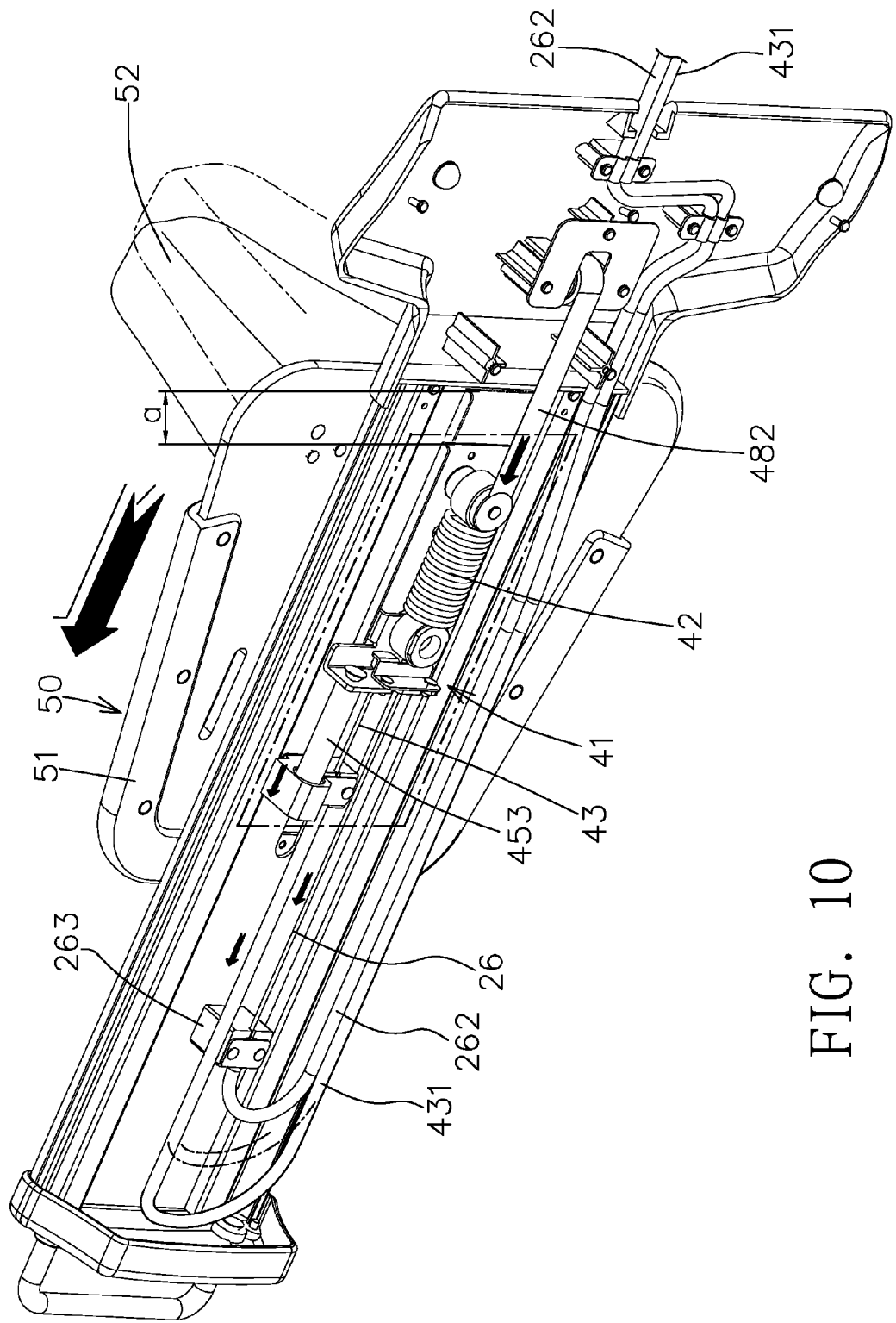
FIG. 10 is a schematic view of a traction operation of the present invention.
Figure 11:
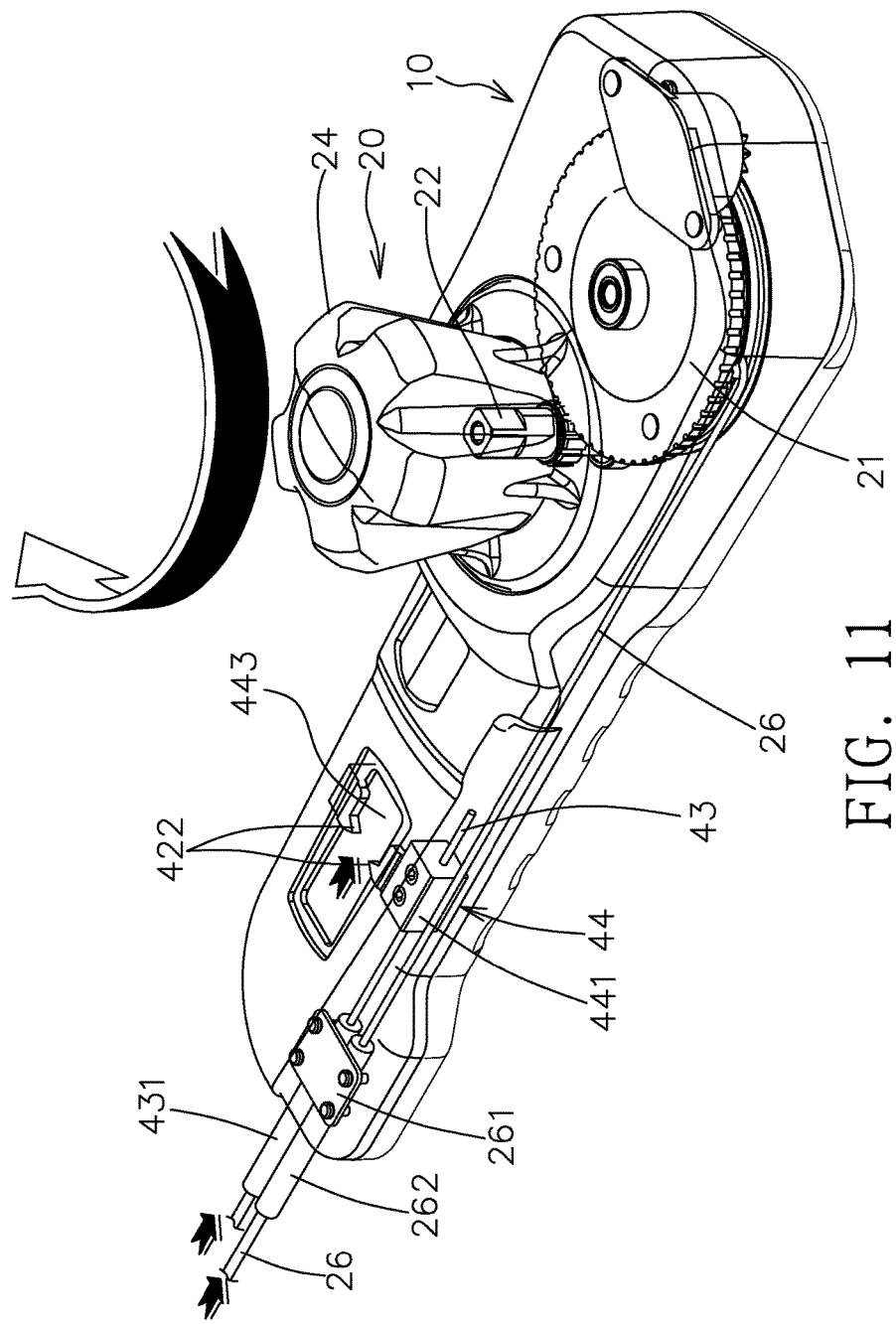
FIG. 11 is a second schematic view of operating and controlling a traction device of the present invention.

In FIGS. 3, 4 and 9, the indicator 44 is installed on the control unit 10 (or the upper controller casing 12), and the indicator 44 includes a display block 441 coupled to and pushed to move by the thrust cable 43. The display block 441 includes a pointer 442, and a viewing panel 443 is installed at the viewing slot 124 provided for showing a reading on the viewing panel 443, so that users may read calibrations, numbers, etc displayed on the viewing panel 443. Of course, the indicator 44 may be a digital indicator that shows a number or a symbol on a screen, and the viewing panel 443 is the screen.

In FIGS. 5 and 6, the transfer unit 50 is slidably installed at the top of the body unit 30 and the transfer unit 50 includes a headrest 51 and a neckrest 52 protruded from the front of the headrest 51, wherein the bottom of the headrest 51 has a connecting portion 511, and the connecting portion 511 (or the headrest 51) is fixed to the linking member 47 (or the load positioning module 41) through the long slot 323 of the upper casing 32 (by screwing as shown in the figure), so that the headrest 51 always moves together with the linking member 47 (or the load positioning module 41), and the bottom of the headrest 51 has a plurality of rollers 512 that can be rolled in the rolling slots 322 on both sides of the upper casing 32 to make the movement of the headrest 51 more smoothly. The neckrest 52 is disposed adjacent to the solder connecting portions 311, 321 and provided for placing a user's neck as shown in FIG. 2.

With reference to FIGS. 2 and 7 to 10 for the traction operation of a traction device for neck physical therapy of the present invention, the pivotal support stand 312 of the body unit 30 is rotated and obliquely set to provide a support effect, and then a user 100 passes the head 101 through the neckrest 52 and rests the head 101 onto the headrest 51, and the user's body leans forward along the solder connecting portion 311, 321 and lies down, and the user 100 may turn the knob 24 of the control unit 10 to apply a force, and then link and rotate the transmission shaft 22 and the transmission disc 21 to link the force applying cable 26, and the force applying cable 26 applies a force to the elastic member 42 through the distal connecting member 45 (or the load positioning module 41). When the buffer strip 482 is pulled to a tense status (in a stroke of the buffer strip), the elastic member 42 will be pulled and stretched to move backward, and then the distal connecting member 45 (or the load positioning module 41) will be pulled to move the thrust cable 43. Now, the headrest 51 (or the transfer unit 50) is linked by the linking member 47 (or the load positioning module 41) to move backward to perform a traction operation and produce a pulling force to the head 101 (or the neck), while the thrust cable 43 is linearly pushing the display block 441 of the control unit 10 to move the pointer 442 of the display block 441 on the viewing panel 443 and allow the user to view and read the traction force related information and numbers.

The traction device for neck physical therapy of the present invention has the following advantages and effects. The users can operate the traction device on their own, and control and fine-tune the traction force easily to provide an excellent controllability of the application. In addition, the present invention allows that users to view a change of data from the viewing panel while performing a traction operation of the traction device for neck physical therapy and use the data as a reference for applying forces in the traction operation or perform an appropriate fine-tune operation of the traction force while viewing the viewing panel, so as to achieve the effects of excellent operability, comfortability, and safety.

What is claimed is:

1. A traction device for neck physical therapy, comprising:
a control unit, including a controller casing;
a knob unit, including a transmission disc, a knob and a force applying cable, and the transmission disc being pivotally installed in the controller casing, and the knob being installed onto the controller casing, and linked to a transmission shaft, and the transmission shaft being linked with the transmission disc, and an end of the force applying cable being fixed to the transmission disc;
a body unit, including a casing comprised of a lower casing and an upper casing;
a force indication unit, including a load positioning module, an elastic member, a thrust cable and an indicator, and the load positioning module being installed in the casing, and the load positioning module being coupled to an end of the force applying cable opposite to the transmission disc, and the elastic member having a first fixing end and a second fixing end, and the first fixing end being fixed to the load positioning module, and the second fixing end being positioned in the body unit, and an end of the thrust cable being coupled to the load positioning module, and the other end of the thrust cable being coupled to the indicator, and the indicator being installed onto the control unit; and
a transfer unit, fixed to the load positioning module and slidably installed on the body unit, the transfer unit includes a headrest, the headrest including a neckrest disposed at the front of the headrest, and a connecting portion disposed at the bottom of the headrest for connecting the load positioning module,
wherein the casing includes a solder connecting portion disposed at an end of the casing and a pivotal support stand coupled to the other end of the casing, and the solder connecting portion is in an outwardly oblique tapered shape,
wherein the upper casing includes a long slot longitudinally penetrated through the upper casing, and the load positioning module is passed through the long slot and coupled to a headrest,
wherein the load positioning module comprises a distal connecting member, a support member and a linking member, and the distal connecting member is coupled to the force applying cable and the thrust cable, and the second fixing end of the elastic member is coupled to the distal connecting member,
wherein the solder connecting portion includes a dolly fixed therein, and the dolly includes a wheel coupled to a buffer strip, and an end of the buffer strip is coupled to the second fixing end of the elastic member,
wherein the indicator includes a display block and a viewing panel coupled to the thrust cable, and the display block is linked to a pointer,
and
wherein when turning the knob of the control unit to apply a force, and then link and rotate the transmission shaft and the transmission disc to link the force applying cable, and the force applying cable applies a force to the elastic member through the distal connecting member, when the buffer strip is pulled to a tense status, the elastic member will be pulled and stretched to move backward, and then the distal connecting member will be pulled to move the thrust cable, now, the headrest is linked by the linking member to move backward to perform a traction operation and produce a pulling force to the head, while the thrust cable is linearly pushing the display block of the control unit to move the pointer of the display block on the viewing panel and allow the user to view and read the traction force related information and numbers.

2. The traction device for neck physical therapy according to claim 1, wherein the controller casing includes a casing perforation formed thereon, and the transmission shaft is pivotally installed in the controller casing and linked by the connection of the casing perforation and the knob, and the controller casing includes an accommodating groove for installing the knob, and a viewing slot.

3. The traction device for neck physical therapy according to claim 2, wherein the knob unit further comprises a positioning plate fixed into the controller casing, and the positioning plate includes a convex positioning seat protruded from the casing perforation and having a shaft hole.

4. The traction device for neck physical therapy according to claim 1, wherein the transmission disc and the transmission shaft respectively have gear ends disposed at peripheries of the transmission disc and the transmission shaft and coupled to each other, and a cable collection slot is formed at the periphery of the transmission disc, and the force applying cable is fixed into the cable collection slot.

5. The traction device for neck physical therapy according to claim 4, wherein the knob unit further comprises a stabilizing member fixed into the controller casing, and the stabilizing member includes a gear member pivotally coupled to the gear end, and the gear member has an elastic resistance.

6. The traction device for neck physical therapy according to claim 4, wherein the knob unit further comprises an elastic pressing member, and the controller casing includes a plurality of positioning notches formed on the elastic pressing member, and an end of the elastic pressing member is abutted against a tooth end of the gear portion of the knob, and the bottom of the elastic pressing member is abutted by a spring.

7. The traction device for neck physical therapy according to claim 1, wherein the upper casing includes a rolling slot formed at the top of the upper casing and separately disposed on both sides of the long slot, and a containing groove is formed separately on both sides of the bottom of the upper casing for providing a cable containing space.

8. The traction device for neck physical therapy according to claim 1, wherein the distal connecting member includes a backwardly protruded pushrod, and the support member includes a pushing groove for containing and abutting the pushrod.

9. The traction device for neck physical therapy according to claim 1, wherein the linking member and the support member are fixed to each other, and the headrest is passed through the long slot and coupled to the linking member.

10. The traction device for neck physical therapy according to claim 1, wherein the upper casing includes a long slot longitudinally penetrated through the upper casing, a rolling slot formed at the top of the upper casing and separately disposed on both sides of the long slot, the headrest includes a plurality of rollers installed at the bottom of the headrest, and the plurality of rollers that be rolled in the rolling slots on both sides of the upper casing to make the movement of the headrest more smoothly.

* * * * *